(12) United States Patent
Xodo et al.

(10) Patent No.: US 9,788,927 B2
(45) Date of Patent: Oct. 17, 2017

(54) SUPPORTING BASE FOR MEDICAL INSTRUMENTS

(71) Applicant: EGMEDICAL S.R.L., I-35010 Villafranca Padovana (IT)

(72) Inventors: Enrico Xodo, Padua (IT); Guido Cappellina, Padua (IT)

(73) Assignee: EGMEDICAL S.R.L., Villafranca Padovana (IT)

( * ) Notice: Subject to any disclaimer, the term of this patent is extended or adjusted under 35 U.S.C. 154(b) by 169 days.

(21) Appl. No.: 14/778,363

(22) PCT Filed: Apr. 2, 2014

(86) PCT No.: PCT/IB2014/060370
§ 371 (c)(1),
(2) Date: Sep. 18, 2015

(87) PCT Pub. No.: WO2014/162272
PCT Pub. Date: Oct. 9, 2014

(65) Prior Publication Data
US 2016/0128793 A1 May 12, 2016

(30) Foreign Application Priority Data

Apr. 4, 2013 (IT) .............................. VR2013A0080
Oct. 16, 2013 (IT) .............................. VR2013A0228

(51) Int. Cl.
*A61C 19/02* (2006.01)
*A61B 50/20* (2016.01)
(Continued)

(52) U.S. Cl.
CPC .............. *A61C 19/02* (2013.01); *A61B 50/20* (2016.02); *A61B 90/08* (2016.02);
(Continued)

(58) Field of Classification Search
CPC ........... A61C 3/04; A61C 19/02; A61B 50/33; A61B 50/20; B29C 45/14344; Y10T 29/49567; Y10T 29/4998
See application file for complete search history.

(56) References Cited

U.S. PATENT DOCUMENTS 5,422,067 A 6/1995 Barney
5,913,422 A 6/1999 Cote et al.
(Continued)

FOREIGN PATENT DOCUMENTS

WO 2012084199 A1 6/2012

*Primary Examiner* — Jermie Cozart
(74) *Attorney, Agent, or Firm* — Pearne & Gordon LLP

(57) ABSTRACT

Described is a supporting base (1) for medical instruments (2), comprising a supporting layer (3) having a relative visible front surface (4) and a relative rear surface (5) opposite the visible surface (4); The supporting layer (3) also has a plurality of holes (6) extending from the front surface (4) towards the rear surface (5); More specifically, the supporting layer has a gripping portion (9) positioned on the rear surface (5) and irreversibly joined to the supporting layer (3) to form a single body with said supporting layer (3). The supporting base (1) has at least one opening (17) for inserting, in use, a medical instrument (2), positioned at each hole (6) and extending from the front surface (4) towards the rear surface (5) and through the gripping portion (9).

15 Claims, 11 Drawing Sheets

(51) Int. Cl.
  *B29C 45/00* (2006.01)
  *B29C 45/14* (2006.01)
  *A61B 90/00* (2016.01)
  *A61C 3/04* (2006.01)
  *B29L 31/00* (2006.01)
  *A61B 50/33* (2016.01)

(52) U.S. Cl.
  CPC .... *B29C 45/0053* (2013.01); *B29C 45/14344* (2013.01); *A61B 50/33* (2016.02); *A61B 2090/0813* (2016.02); *A61C 3/04* (2013.01); *B29C 2045/14868* (2013.01); *B29L 2031/753* (2013.01); *Y10T 29/4998* (2015.01); *Y10T 29/49567* (2015.01)

(56) References Cited

U.S. PATENT DOCUMENTS

| | | | |
|---|---|---|---|
| 6,193,932 B1* | 2/2001 | Wu | A61L 2/07 206/210 |
| 2006/0272979 A1* | 12/2006 | Lubbers | A61B 50/20 206/557 |
| 2007/0138042 A1 | 6/2007 | Wood | |
| 2008/0149512 A1* | 6/2008 | Dane | A61L 2/26 206/370 |
| 2012/0094249 A1* | 4/2012 | Abene | A61C 19/02 433/77 |
| 2012/0273446 A1 | 11/2012 | Moore | |
| 2013/0334083 A1 | 12/2013 | Bugnard et al. | |

\* cited by examiner

SUPPORTING BASE FOR MEDICAL INSTRUMENTS

TECHNICAL FIELD

This invention relates to a supporting base for medical instruments and a method for making the supporting base.

BACKGROUND ART

More specifically, the supporting base of this invention lies in the technical field of supports for medical instruments.

In effect, in the medical sector, it is often necessary to have supporting bases on which the medical instruments are positioned. More specifically, these supporting bases allow the instruments necessary to perform predetermined operations to be held and made available to the doctor (preferably "near to hand").

In detail, this invention is preferably used in the dental treatment sector, where it is necessary to provide the dentist with various types of instruments. In practice, the supporting base holds the instruments which the dentist believes it is worthwhile having available. In any case, this invention is part of what is commonly called: "surgical kit".

According to the prior art, a supporting base for medical instruments is formed by a rigid plate on which a plurality of through holes are made. In addition, the rigid plate has a surface on view and a rear surface opposite the surface on view.

More specifically, at each through hole a respective gripping ring is inserted which defines a narrowing of the hole in such a way as to form a passage cross-section which is able to retain a specific medical instrument. In other words, each gripping ring defines inside it a passage in which the medical instrument is held. The gripping ring is preferably made of silicone rubber in such a way as to grip the instrument which is inserted inside.

More specifically, each gripping ring partly superposes the front surface and the lower surface of the rigid plate, in such a way that they remain in position. In other words, the gripping ring has externally an intermediate cavity with an annular shape housing the edge defining the respective hole of the plate once the gripping ring has been inserted.

In addition, the gripping ring is positioned in the hole by an operation for deformation of the ring in such a way as to form a mechanical locking on the plate.

Further, each gripping ring may have protrusions inside, of various shapes and types, which favour the retaining of the medical instrument inside the passage.

During use, the rigid plate (normally supported by suitable feet) is placed on a work table and the various medical instruments are inserted in the holes (extending at right angles to the surface area of the plate).

However, this prior art technique has several drawbacks.

More specifically, the main drawback is linked to the fact that dirt can accumulate between the gripping ring and the plate which favours the proliferation of microbes, harmful bacteria, etc. Still more specifically, the dirt enters the gaps present between each gripping ring and the underlying hole.

For example, in the dental treatment sector, it often happens that the instruments are soiled with blood, water and saliva and that they are inserted in and removed from the plate several times during a dental operation. For this reason, these substances accumulate on the plate creating, over time, a surface for proliferation of bacteria and the like. Consequently, it is necessary to clean the plate regularly in order to prevent the formation of microbes which can corrode the instruments. However, the procedure for cleaning the plate is particularly difficult because the surfaces of the plate are not smooth surfaces, but comprise a plurality of obstacles due to the protrusions created by the various sealing rings. For this reason, for the cleaning it is necessary to remove the sealing rings, clean the surfaces of the plate and clean the sealing rings.

However, this operation is difficult and slow. In addition, each gripping ring, as it is made of rubber, tends to trap the dirt making its removal often impossible.

In addition, it should be noted that the making of the base is often a complicated operation as a whole. In effect, during manufacture, it is necessary to make the gripping rings separate from the plate and join the gripping rings to the plate at a subsequent time

DISCLOSURE OF THE INVENTION

In this situation, the aim of this invention is to provide a supporting base for medical instruments which overcomes the above-mentioned drawbacks.

More specifically, the aim of this invention is to provide a supporting base which facilitates the operations for cleaning the surfaces of the supporting base.

Another aim of this invention is to provide a supporting base which simplifies the operations for making the supporting base.

The aims indicated are substantially achieved by a supporting base as described in the appended claims.

BRIEF DESCRIPTION OF THE DRAWINGS

Further features and advantages of the invention are more apparent from the detailed description which follows of a preferred but non-limiting embodiment of a supporting base as illustrated in the accompanying drawings, in which.

DETAILED DESCRIPTION OF THE PREFERRED EMBODIMENTS OF THE INVENTION

Figure 1:
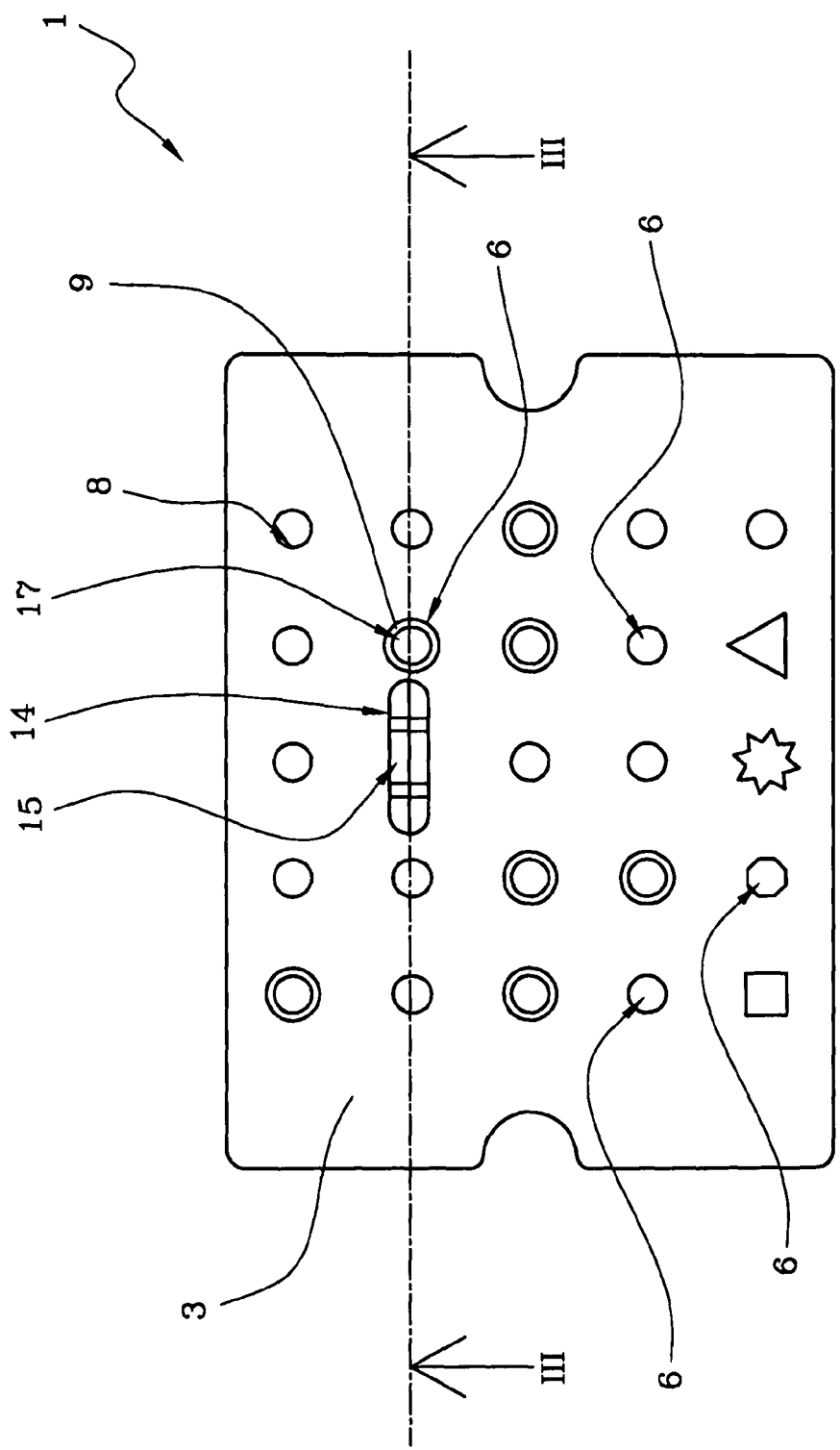
FIG. 1 is a top view of a supporting base in a first embodiment of this invention.

More specifically, the supporting base 1 comprises a supporting layer 3 extending along a relative surface area. In the first preferred embodiment illustrated for example in FIG. 3, the supporting layer 3 has a substantially planar extension. In other words, the supporting layer 3 is substantially plate-shaped and supports the medical instruments 2 positioned on it.

The supporting layer 3 has a relative front surface 4 on view and a relative rear surface 5 opposite the surface on view. More in detail, the front surface 4 is, in use, is facing upwards, whilst the rear surface 5 is, in use, facing downwards. In effect, during the use of the supporting base 1, the supporting layer 3 extends substantially parallel, or at least partly inclined, to a supporting surface 100 on which the supporting base 1 is positioned. The supporting layer 3 has a plurality of through holes 6 extending from the front surface 4 to the rear surface 5 for inserting, in use, respective medical instruments 2 so as to make a support for them. In other words, each hole 6 extends transversely (preferably at right angles) to the surface area of the supporting layer 3 in such a way that a respective medical instrument 2 can be inserted inside the hole 6 following a direction of insertion 7 at a right angles to the surface area of the supporting layer 3. In other words, each hole 6 extends from the front surface 4 to the rear surface 5 along the direction of insertion 7.

Figure 4:
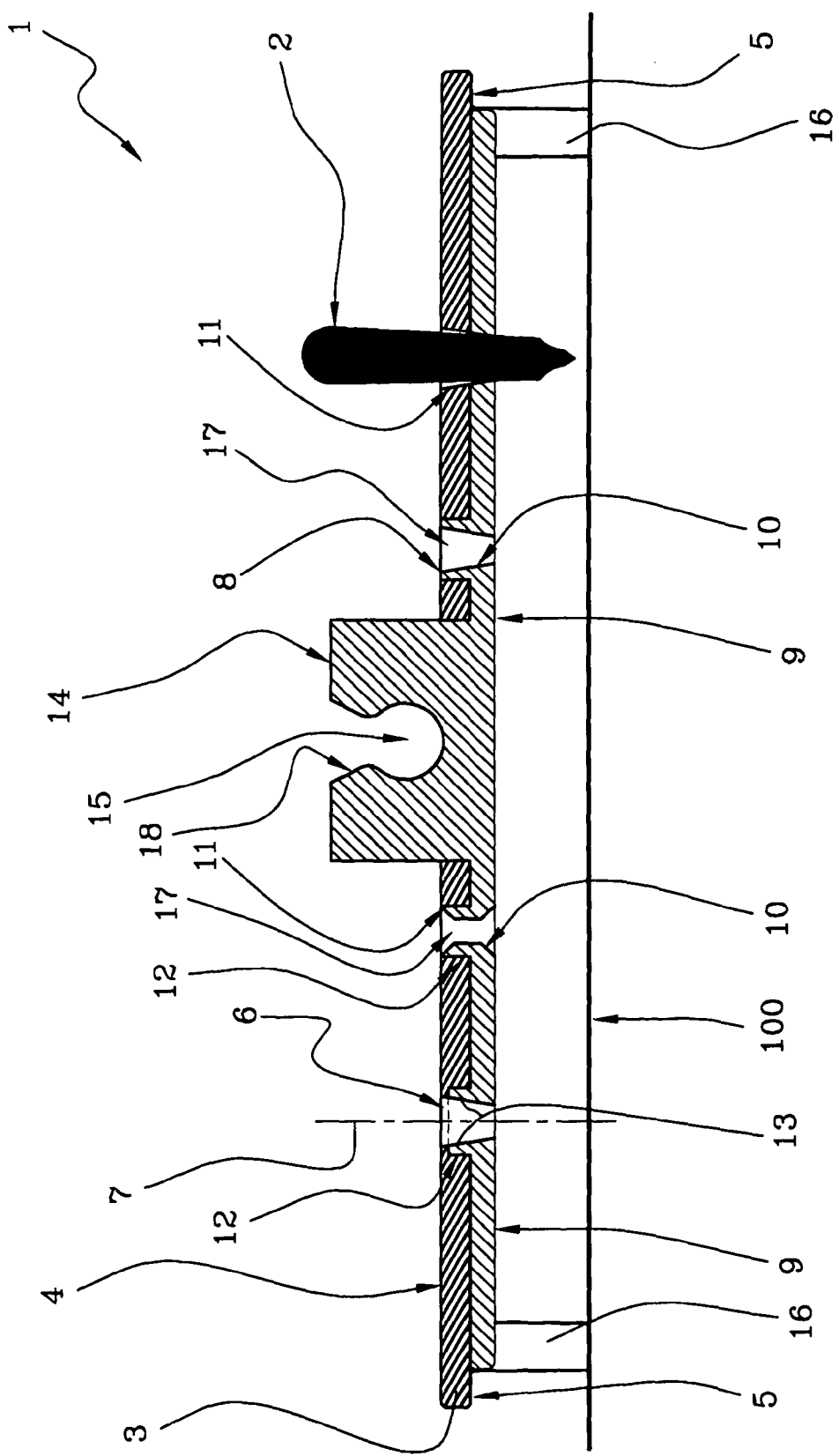
FIG. 4 is a side view of a first variant embodiment of the supporting base of FIG. 3.

FIG. 4 illustrates, by way of example, a medical instrument 2 inserted in one of the above-mentioned holes 6. As may be seen in the drawing, a medical instrument 2, in turn inserted in the hole 6, remains hanging from the supporting base 1.

Moreover, each hole 6 has a respective predetermined containment shape for inserting a respective medical instrument 2.

The containment shape refers to the shape defined by the edges 8 of the hole 6 on a lying plane (transversal to the direction of insertion 7 previously defined) of the hole 6.

Figure 2:
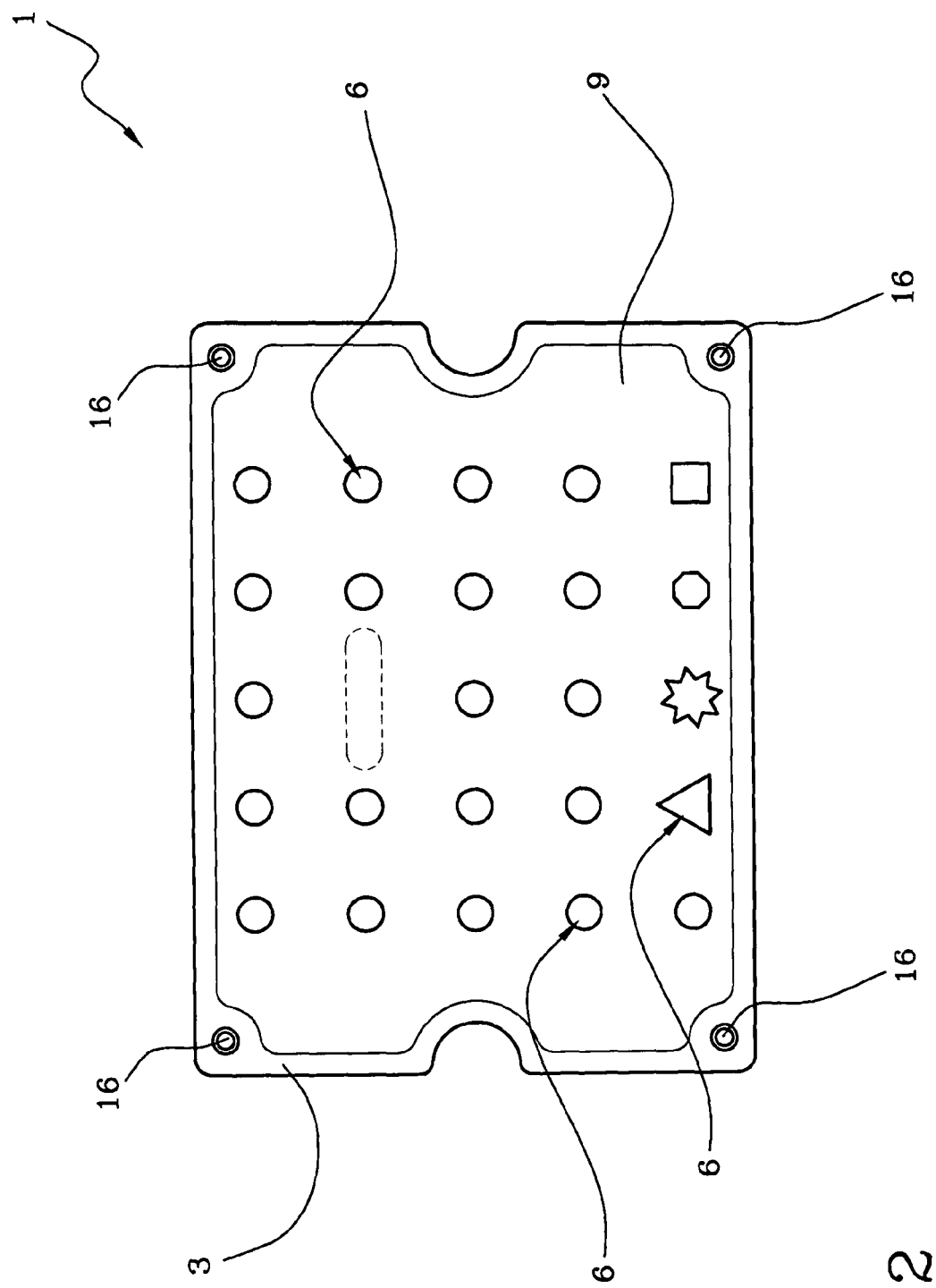
FIG. 2 is a bottom view of the supporting base of FIG. 1.

For example, FIGS. 1 and 2 show holes 6 of circular, rectangular, triangular, star and pentagonal shapes.

Moreover, each hole 6 may have an internal shape along the direction of insertion 7 as a function of the needs linked to the shape and size of a medical instrument 2 to be inserted. The internal shape refers to the projection from the annular surface of the hole 6 on a plane at right angles to the lying plane of the hole 6 (parallel to the direction of insertion 7 previously defined) and passing through the hole 6.

Further, each hole 6 has a width L (measured along a plane in which the hole 6 lies) predetermined according to the dimensions of the medical instrument 2 to be inserted. More specifically, the width L of a hole 6 may be constant or variable along the direction of insertion 7 according to the dimensions of the medical instrument 2 to be inserted.

It should be noted that the term "supporting layer 3" means a layer comprising material capable of giving mechanical support to the medical instruments 2. In other words, the supporting layer 3 is a layer of rigid material. Preferably, the supporting layer 3 comprises plastic material. Even more preferably, the supporting layer 3 is made of plastic.

In accordance with this invention, the supporting base 1 comprises a gripping portion 9 extending along the surface area. In other words, the gripping portion 9 extends substantially parallel to the supporting layer 3. Preferably, the gripping portion 9 comprises gripping material capable of making a gripping action on the medical instrument 2.

Moreover, the gripping portion 9 is joined to the supporting layer 3 only at the rear surface 5 in such a way as to form a single body with the supporting layer 3. In other words, the supporting base 1 is a single body comprising two layers joined to each other: the supporting layer 3 and the gripping portion 9.

It should be noted that the front surface 4 of the supporting layer 3 is preferably smooth in such a way as to favour the surface cleaning operations.

Moreover, the supporting layer 3 and the gripping portion 9 are co-pressed together in such a way as to form a single body. Alternatively, the supporting layer 3 and the gripping portion 9 are joined together by means of known techniques which allow the irreversible joining of two materials (for example: casting, etc.)

In addition, each of the holes 6 extends along the direction of insertion 7 inside the gripping layer in such a way as to form an annular gripping area 10 for a respective medical instrument 2 inserted in the hole 6. Preferably, as shown in the accompanying drawings, the gripping layer is perforated at the holes 6 in such a way that the latter pass through the gripping portion 9. In other words, each hole 6 passes through the supporting layer 3 and the gripping portion 9.

In this way, each hole 6 is formed by an annular inner surface comprising an annular passage area 11, formed by the supporting layer 3, and an annular gripping area 10 formed by the gripping portion 9. In this way, when a medical instrument 2 is inserted in a respective hole 6, it first passes through (leading from the front surface 4 to the upper surface) the annular passage area 11 and then the annular gripping area 10.

Preferably, the gripping portion 9 comprises rubber. Even more preferably, the gripping portion 9 comprises silicone rubber. More in detail, the gripping portion 9 contains silicone.

Advantageously, the plastic of the supporting layer 3 and the silicone of the gripping portion 9 lend themselves to the co-pressing process.

Figure 3:
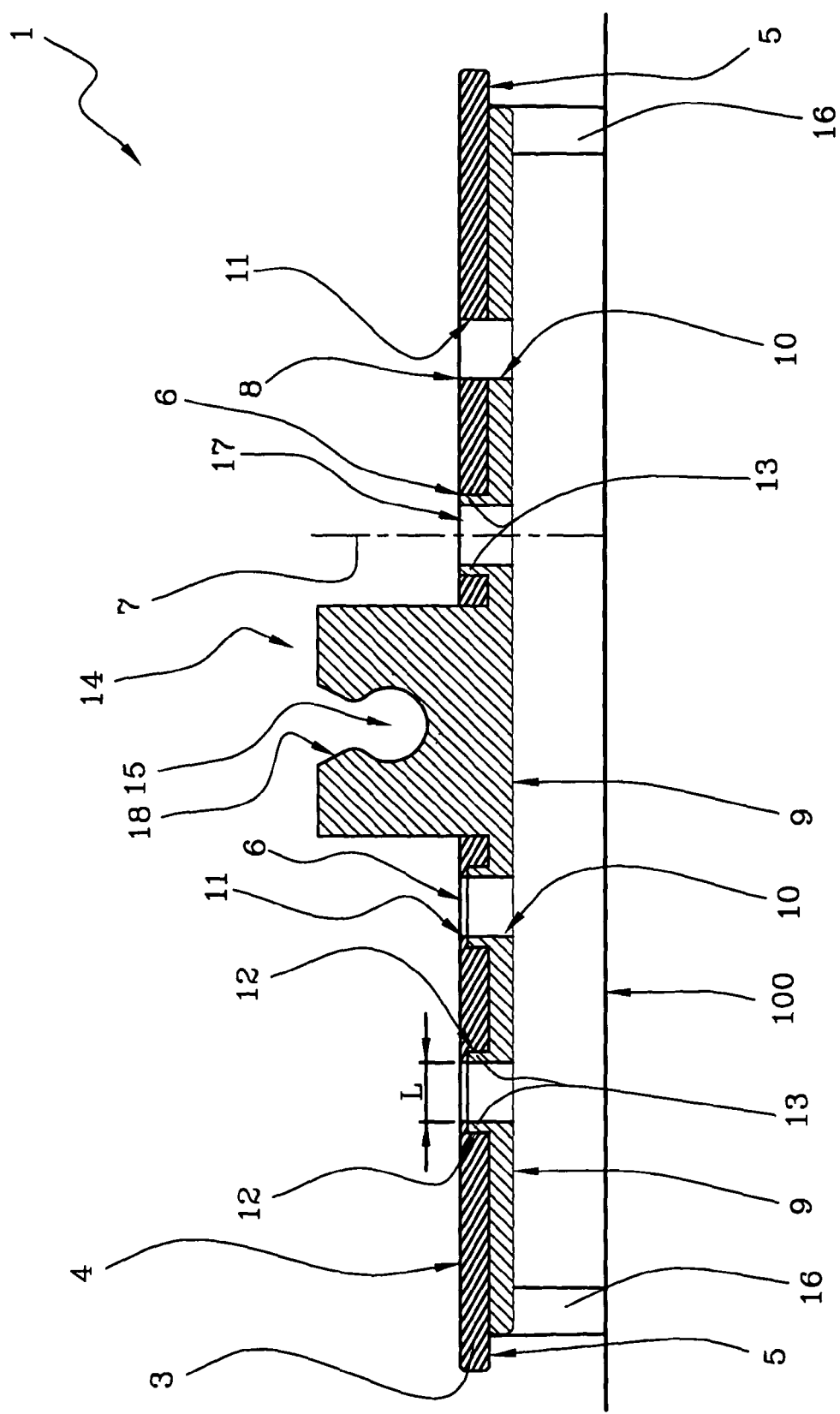
FIG. 3 is a side view of the supporting base of FIG. 1 in a cross-section through the line III-III.

Moreover, in the embodiments illustrated in FIGS. 3 and 4 the gripping portion 9 extends, at least partly, inside at least one hole 6 towards the front surface 4 in such a way as to form a coating inside the hole 6. In other words, the gripping portion 9 comprises protuberances 13 each extending inside a respective hole 6 for a predetermined height. Each protuberance 13 is internally perforated as an extension of the respective hole 6. In other words, each protuberance 13 has a respective opening 17 passing through the gripping portion 9 for inserting the medical instrument 2. In yet other words, as explained in more detail below, the coated hole 6 has inside at least one opening 17 for inserting a medical instrument 2.

In these embodiments, the hole 6 has an annular recess 12, extending from the rear surface 5 towards the front, in which the extended part of the gripping material is inserted.

Preferably, gripping portion 9 extends inside the hole 6 for the entire length of the latter up to the front surface 4 in such a way as to completely coat the hole 6 with the gripping material.

In the latter case, it should be noted that the gripping portion 9 is aligned at the top with the front surface 4 in such a way as to define a surface free from obstacles and substantially smooth. In that case, the annular surface inside the hole 6 is formed entirely by the gripping material.

In any event, each opening 17 may have an internal shape along the direction of insertion 7 (as a function of the needs linked to the shape and size of a medical instrument 2) irrespective of the internal shape of the respective hole 6. The internal shape refers to the projection from the annular surface of the opening 17 on a plane at right angles to the lying plane of the hole 6 (substantially parallel to the direction of insertion 7 previously defined) and passing through the hole 6.

By way of example, the internal shape of the openings 17 shown in Figure is of the cone type and forms a narrowing from the front surface 4 to the rear surface 5 in such a way as to favour the retaining of a medical instrument 2 inside the respective opening 17.

According to another embodiment shown in FIG. 4 (second hole 6 from left) the internal shape of the opening 17 is defined by a double cone, of which one inverted, and forms, along the direction of insertion 7, a narrowing of the cross-section from the front surface 4 towards the rear surface 5 and a subsequent widening of the cross-section towards the gripping portion 9 following the direction of insertion 7. Advantageously, the internal shape of the opening 17 facilitates the insertion of a medical instrument 2 in the hole through the front surface 4 and, at the same time, the removal of the same medical instrument 2 from the opening 17.

Figure 5:
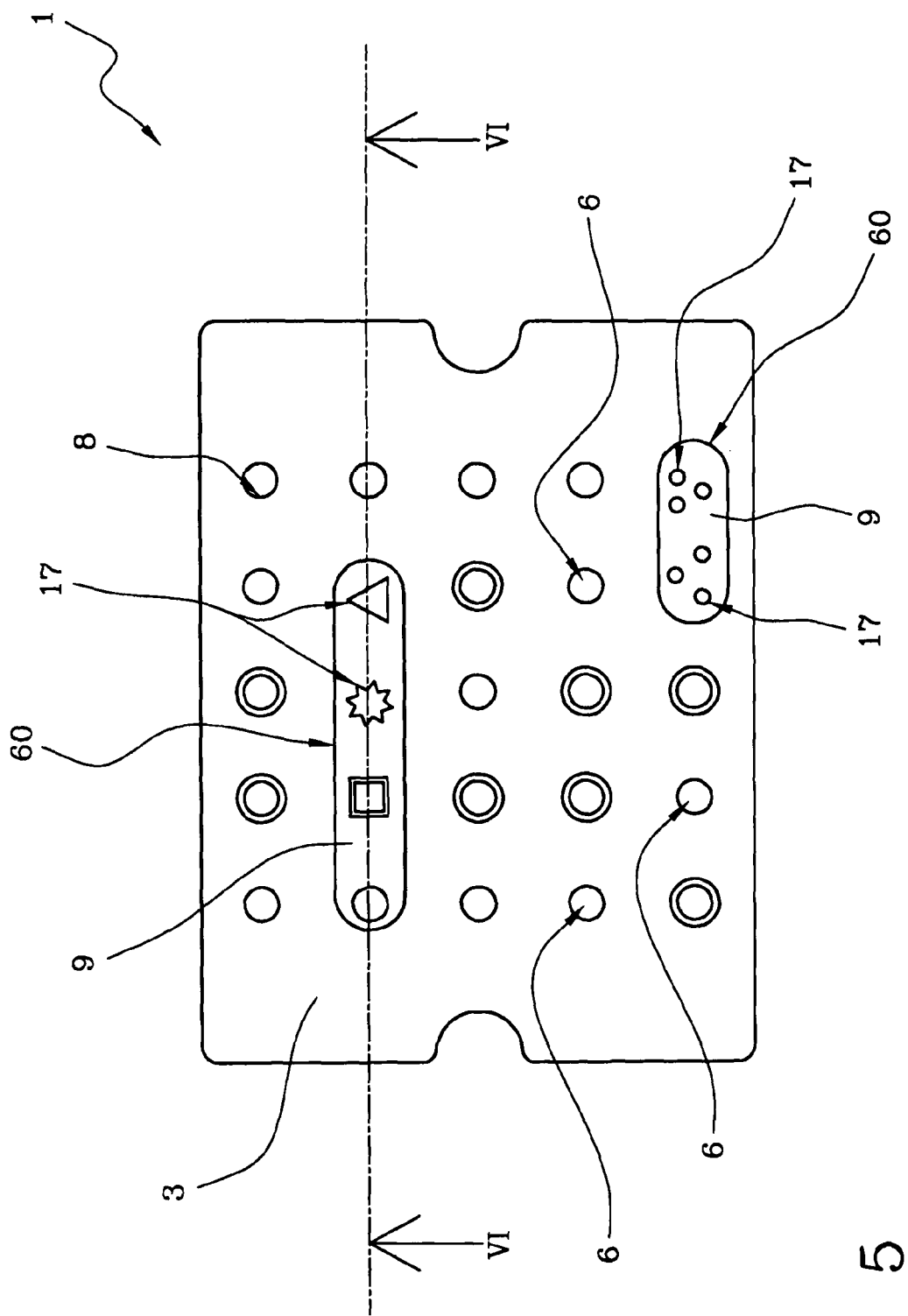
FIG. 5 is a top view of a second variant embodiment of the supporting base of FIG. 1.

In the variant embodiment of FIG. 5, the layer of supporting material 3 has an elongate hole 60 extending from the front surface 4 to the rear surface 5 in which the gripping portion 9 extends. In other words, the elongate hole 60 is basically a hole 6 having a greater extension along the surface area of the layer of supporting material 3.

More in detail, the gripping portion 9 extends inside the elongate hole 60 for the entire length of the latter up to the front surface 4 in such a way as to completely coat the inside of the hole 60 with the gripping material. In other words, the gripping portion 9 extends inside the elongate hole 60 defining an elongate protuberance 13.

Figure 6:
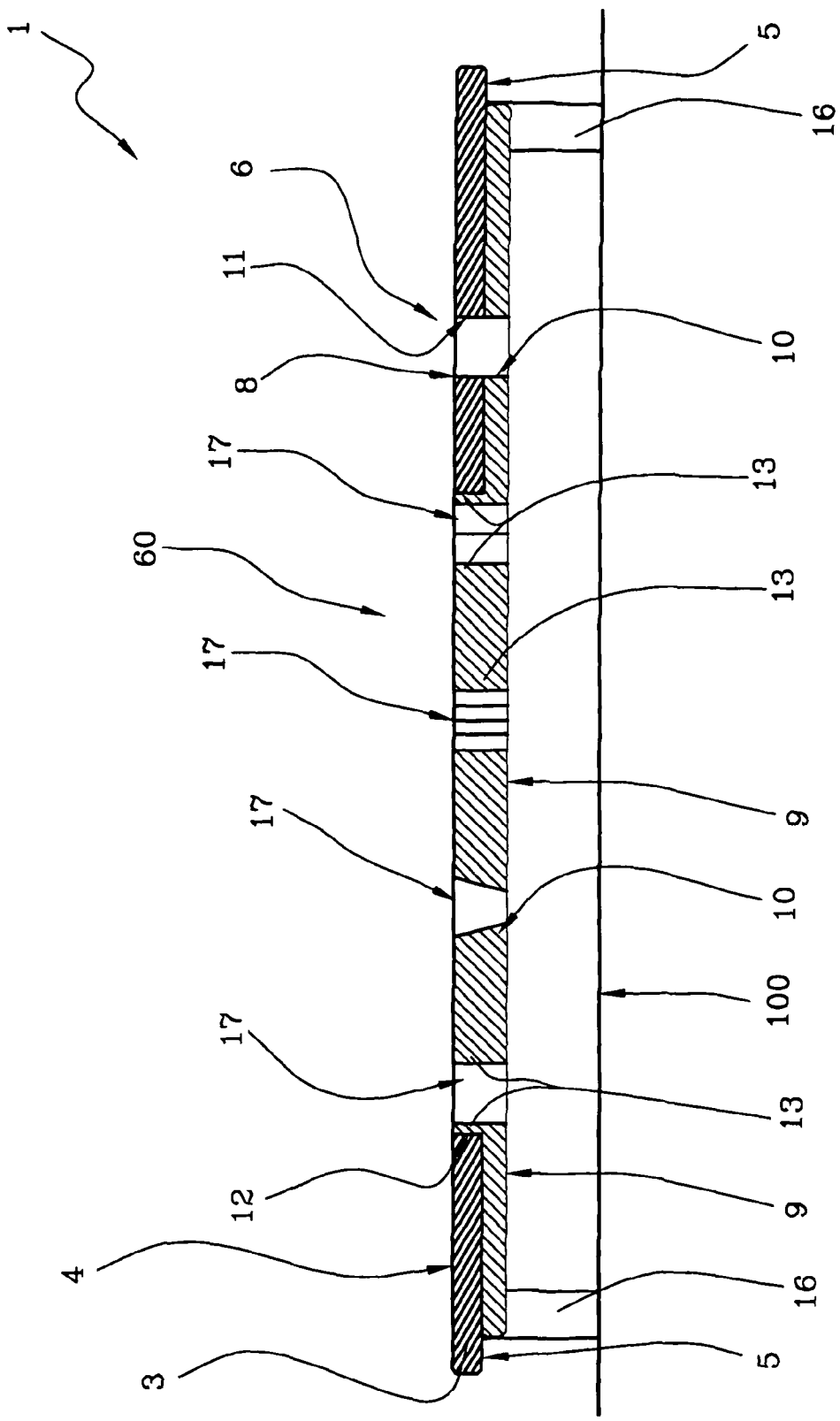
FIG. 6 is a side view of the supporting base of FIG. 5 in a cross-section through the line VI-VI.

In that case, in the same way as explained above, the elongate protuberance 13 has a plurality of through openings 17 through the gripping portion 9 for inserting the medical instrument 2. As shown in FIGS. 5 and 6, each of these openings 17 may have shape and dimensions which are predetermined and different to each other (as described above for the holes 6) irrespective of the shape and size of the elongate hole 60.

Moreover, as may be seen from the central part of the supporting base 1 illustrated in FIGS. 1 and 3, the gripping layer extends all the way through a respective hole 6 and projects from the front surface 4 so as to define a protruding gripping portion 14. The protruding gripping portion 14 rises from the front surface 4 and is shaped to form a cavity 15 for containing a medical instrument 2.

In that way, it is possible to define a cavity 15 for containing a medical instrument 2 in a raised position relative to the front surface 4. More specifically, the protruding gripping portion 14 has a top wherein a containment cavity 15 is made. Preferably, the containment cavity 15 has an extension substantially parallel to the front surface 4 in such a way as to contain a medical instrument 2 positioned along the extension.

It should be noted that the gripping portion 14 has, at the top, a guide profile 18 placed in communication with the containment cavity 15. More specifically, the guide profile 18 is shaped like an inverted truncated cone to favour the insertion of a medical instrument 2 in the containment cavity 15. The guide profile 18 extends between an upper opening (for the entrance of the medical instrument 2) and a lower opening having a diameter less than the upper opening. More in detail, the lower opening is interposed between the rest of the guide profile 18 and the containment cavity 15 and forms a narrowing of the cross section relative to the containment cavity 15 in such a way as to hold the medical instrument 2 in position once it has passed the lower opening.

Lastly, as shown in FIGS. 3 and 4, the supporting base 1 comprises supporting means 16 connected to the supporting layer 3 and extending away from it in such a way as to support the rest of the supporting base 1. Preferably, the supporting means 16 comprise a plurality of supporting feet extending away from the supporting layer 3 for a predetermined length in such a way as to support the supporting layer 3.

With reference to the second embodiment illustrated in FIGS. 7 to 11, the reference numeral 1 again denotes the supporting base device according to this invention.

More specifically, in the second embodiment the gripping portion 9 is positioned on the rear surface 5 and extends along a predetermined path passing through at least one group 31 of holes 6. The gripping portion 9 is positioned inside the holes 6 of the group 31 in such a way as to fill them. In other words, the gripping portion 9 is positioned on the rear surface 5 along a predetermined path (and does not cover the entire rear surface 5 as in the first embodiment).

Preferably, the supporting layer 3 has a track 30 cut in the rear surface 5 extending along a predetermined path and passing through at least one group 31 of holes 6 in order to place them in communication with each other through the track 30. In other words, the supporting layer 3 has a cut which extends along the predetermined path in such a way as to define a through track 30 for the holes 6 of the group 31. In yet other words, the holes 6 of the group 31 are made along the predetermined path of the track 30.

It should be noted that the track 30 has a depth, measured from the rear surface 5 towards the front surface 4, less than the thickness of the supporting layer 3. In that case, the track 30 does not pass through the supporting layer 3.

In some alternative embodiments not illustrated in the accompanying drawings, the track 30 is formed by a slot passing through the entire thickness of the supporting layer 3.

Figure 10:
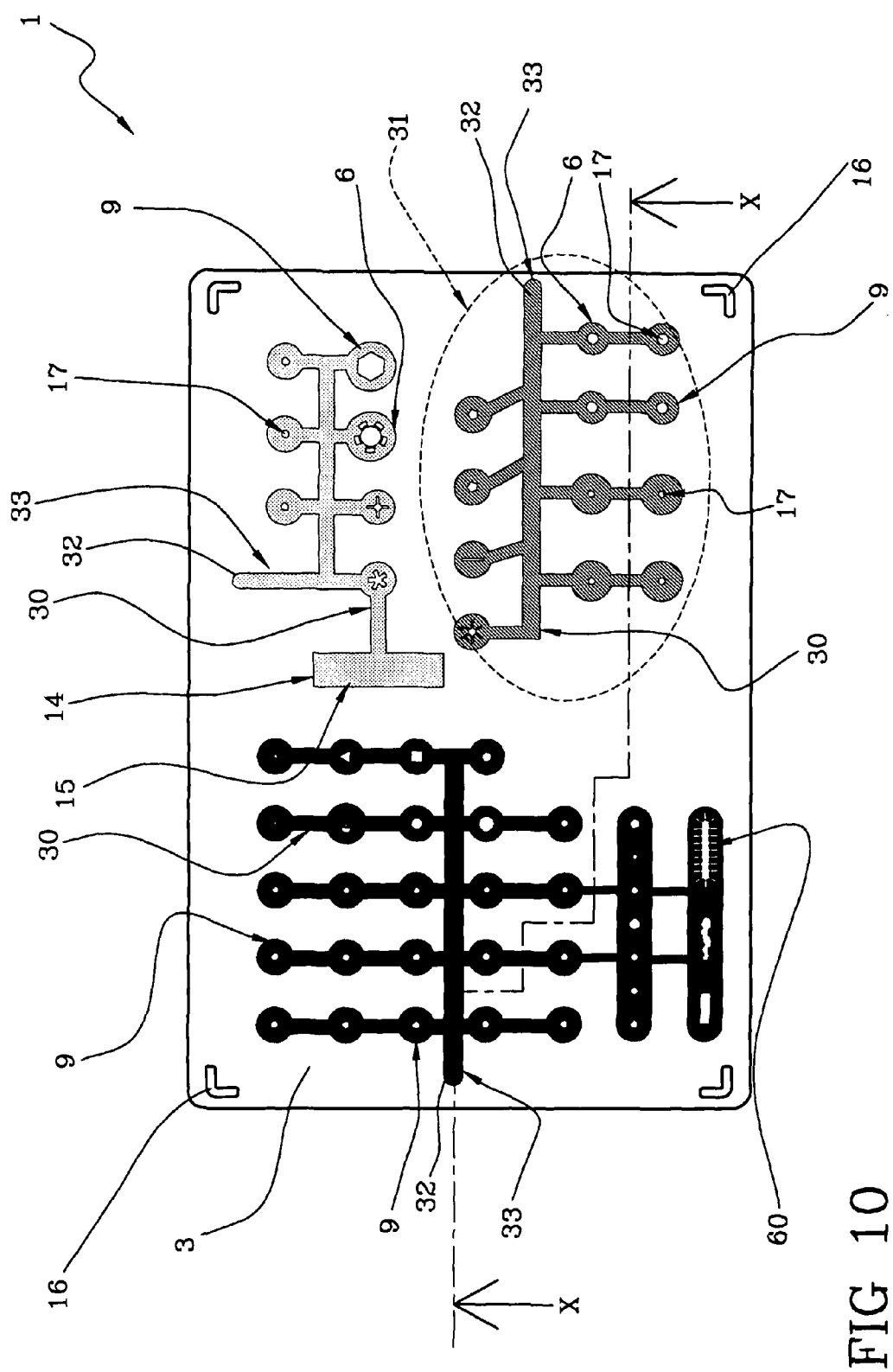
FIG. 10 is a bottom view of the supporting base of FIG. 7.

Moreover, in the preferred embodiment illustrated, for example, in FIG. 10, the track 30 has a width, measured transversely to the predetermined path, less than the diameter of a hole 6. However, in other embodiments not illustrated in the accompanying drawings, the track 30 might have a width equal to or greater than the diameter of a hole 6.

Figure 11:
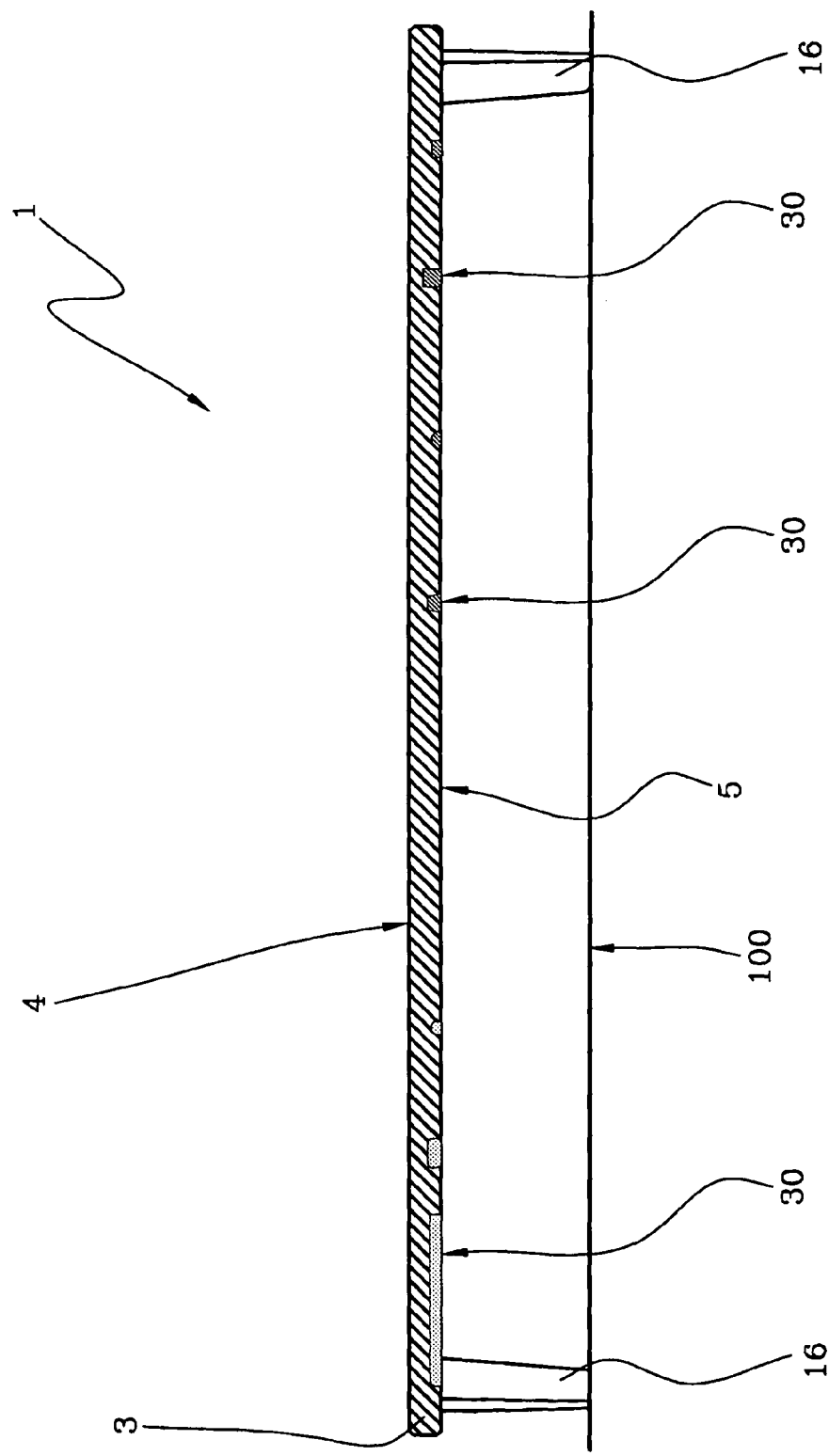
FIG. 11 is a side view of the supporting base of FIG. 10 in a cross-section through the line X-X.

In addition, the track has a respective cross-section (in a plane positioned at a right angle to the surface area of the supporting layer 3) which may comprise various shapes depending on requirements. More specifically, FIG. 11 shows that the cross-section of the track 30 may comprise, also for parts relating to a same group 31, rectangular and/or square and/or semi-circular and/or oval shapes and/or other shapes not expressly described herein.

Moreover, the gripping portion 9 is positioned inside the track 30 and at each hole 6 of the group 31. In other words, the gripping portion 9 is positioned inside the track 30 and follows the trend in such a way as to form gripping portions 9 at the holes 6. In yet other words, the gripping portion 9 fills the cut present on the rear surface 5 and the holes 6.

It should be noted that, in the second preferred embodiment illustrated in the accompanying drawings, the gripping portion 9 is inserted, at least partly, inside the track 30.

In other embodiments where the cut track 30 is not present, the gripping portion 9 is connected to the rear surface 5 and protrudes from it towards the outside.

Preferably, the gripping portion 9 also extends inside each hole 6 of the group 31 up to the front surface 4.

In the second embodiment illustrated in the accompanying drawings, there is a plurality of tracks 30 which are separate from each other that put in communication respective groups 31 of holes 6. More in detail, the accompanying drawings show that the supporting base 1 comprises three tracks 30 and three groups 31 of holes 6 each of the groups being associated with a respective track 30.

In some alternative embodiments not illustrated in the accompanying drawings, the supporting base 1 comprises a single track 30 extending at all the holes 6 in such a way that the latter are in communication with each other through the single track 30.

As already mentioned for the first embodiment, the gripping portion 9 is made of a gripping material to form an annular gripping area inside the hole 6. Preferably, the gripping material comprises rubber. Even more preferably, the gripping material comprises silicone rubber. More in detail, the gripping material contains silicone.

In addition, the gripping portion 9 is joined to the supporting layer 3 also at the inner surface 20 in such a way as to form a single body with the supporting layer 3. Preferably, the gripping portion 9 is joined to the supporting layer 3 in a permanent fashion. In other words, the supporting base 1 is a single body comprising two parts joined to each other: the supporting layer 3 and the gripping portion 9.

In other words, the gripping portion 9 coats the inner surface 20 of the supporting layer 3 at each hole 6 in such a way as to form an annular gripping area. In yet other words, the gripping portion 9 extends from the inner surface 20 towards the hole 6 along a direction transversal (preferably orthogonal) to the direction of insertion 7.

Preferably, the gripping portion 9 covers the entire annular inner surface 20 of each hole 6.

As already mentioned, each coated hole 6 defines internally at least one opening 17 for insertion of a medical instrument 2. In practice, the opening 17 defines a narrowing of the hole 6.

It should also be noted that, as shown in the accompanying drawings, one or more gripping portions 9 have different colours from at least one other gripping portion 9 to distinguish at least one opening 17 from another (the various colours are represented in the drawings by different tones of grey). More specifically, as shown in FIG. 10, the gripping portion 9 of a group 31 has a same colour. Whilst gripping portions 9 of different groups have different colours. In effect, advantageously, each gripping portion 9 is made from a single casting of gripping material and, therefore, has a single colour.

More in detail, the colour of the gripping portion 9 is used to distinguish the openings 17 of a group 31 from the openings of another group 31. In that way, it is possible to reduce the positioning error of an instrument 2 in the openings of a group 31 relative to those of another group since each opening 17 of a group 31 may have features which are specific and different from the others as defined below. For this reason, since these specific features are difficult to distinguish with the naked eye, the various colours of the gripping portions 9 facilitate the correct positioning of the instruments 2 in the respective opening 17 by the operator.

Alternatively, the gripping portions 9 may have the same colour.

Further, each opening 17 has a width S (measured along a plane in which the hole 6 lies) predetermined according to the dimensions of the medical instrument 2 to be inserted. More specifically, the width S of the opening 17 may be constant or variable along the direction of insertion 7 according to the dimensions of the medical instrument 2 to be inserted.

Moreover, as shown in the accompanying drawings, the openings 17 have respective containment shapes which are predetermined and different from each other depending on the shape of the medical instrument 2.

Figure 7:
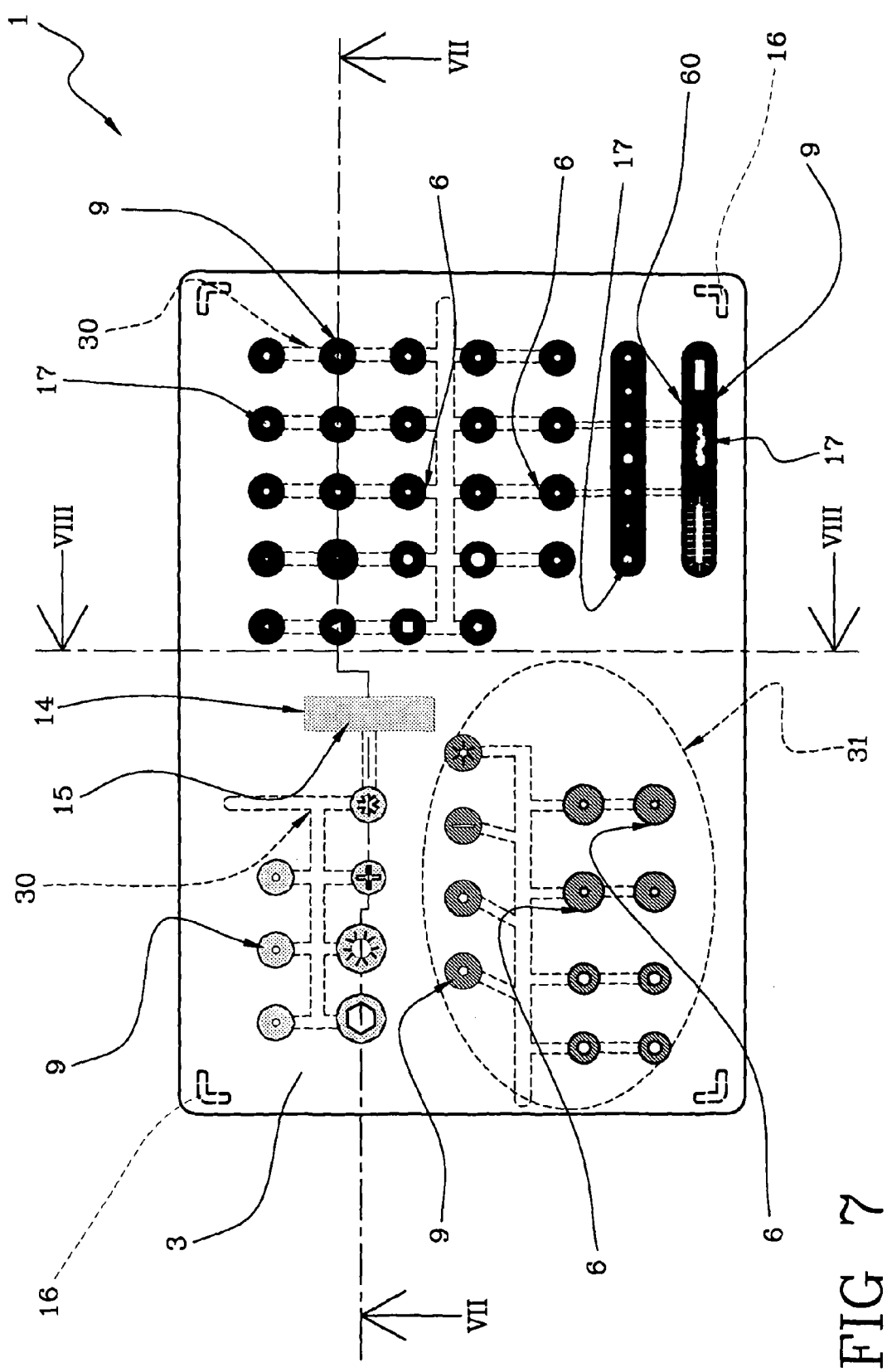
FIG. 7 is a top view of a supporting base according to a second embodiment of this invention.

It should be noted that the containment shape of each opening 17 refers to the shape defined by the edges of the opening 17 on a lying plane (at right angles to the direction of insertion 7 previously defined) of the opening 17. For example, FIG. 7 shows openings 17 of circular, rectangular, triangular, star and pentagonal shapes, etc.

Moreover, each opening 17 may have an internal shape along the direction of insertion 7 as a function of the needs linked to the shape and size of a medical instrument 2 to be inserted. The internal shape is defined by the contour lines of the opening 17 sectioned with a plane at right angles to the lying plane of the opening 17 (parallel to the direction of insertion 7 previously defined) and passing through the respective hole 6. By way of example, the internal shape of some openings 17 shown in FIG. 9 is of the cone type and forms a narrowing from the front surface 4 to the rear surface 5 in such a way as to favour the retaining of a medical instrument 2 inside the respective hole 6.

Figure 9:
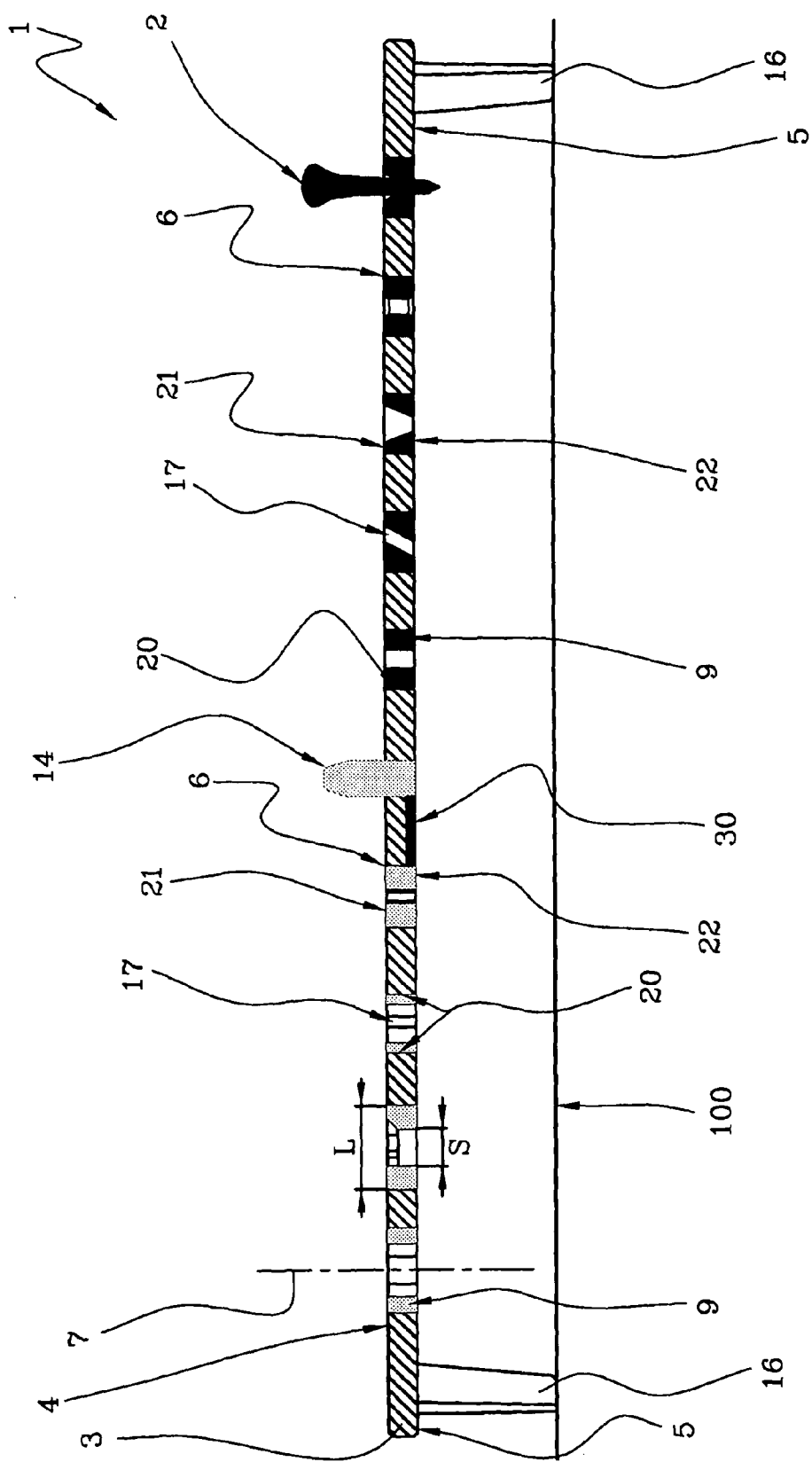
FIG. 9 is a side view of the supporting base of FIG. 7 in a cross-section through the line VII-VII.

According to another embodiment shown in FIG. 9 (second hole 6 from right) the internal shape of the opening 17 is defined by a double cone, of which one inverted and spaced from the other, and forms, along the direction of insertion 7, a narrowing of the cross-section from the front surface 4 towards the rear surface 5 and a subsequent re-widening of the cross-section close to the rear surface 5 following the direction of insertion 7. Advantageously, the internal shape of the opening 17 facilitates the insertion of a medical instrument 2 in the hole 6 through the front surface 4 and, at the same time, the removal of the same medical instrument 2 from the opening 17.

It should be noted that each hole 17 extends, from the front surface 4 to the rear surface 5, along the direction of insertion 7 of the respective hole 6 substantially parallel to it or along a direction inclined to it. In other words, the opening 17 may to extend along a respective direction of extension irrespective of the direction of insertion 7 along which the respective hole 6 extends. In yet other words, the opening 17 can extend along a relative direction of extension inclined, at an angle different from the right angle, with respect to the surface area of the supporting layer 3 positioned at the opening 17.

For example, the fourth opening 17 from the right in FIG. 9 (corresponding to the fourth opening 17 from the left of the second line from the top in FIG. 10) extends from the front surface 4 to the rear surface 5 along a direction inclined relative to the direction of insertion 7. In addition, in some embodiments of openings 17, the gripping portion 9 defines a plurality of openings 17 passing inside the same hole 6 for insertion of a medical instrument 2 for each opening 17. In that case, the gripping portion 9 extends inside the hole 6 along the entire inner surface 20 in such a way as to completely coat the inside of the hole 6 with the gripping material.

Preferably, in this case, the hole 6 is elongate in shape (elongate hole 60) (that is, the surface area of the hole 6) in which the gripping portion 9 extends. Obviously, the containment shape and the internal shape of each opening 17 made in the same hole 6 is independent of the shape and dimensions of the hole 6.

Moreover, the gripping portion 9 extends along the direction of insertion 7 from its own rear face 22, positioned at the rear surface 5, to its own front face 21, positioned at the front surface 4. Preferably, the front face 21 is aligned with the front surface 4 in such a way as to form, in its entirety, a continuous surface. In other words, the gripping portion 9 is aligned at the top with the front surface 4 in such a way as to define a surface free from obstacles and substantially smooth.

In that way, the surface cleaning operations for the supporting base 1 are favoured.

Moreover, the front surface 4 of the supporting layer 3 is preferably smooth in such a way as to favour even more the surface cleaning operations.

In addition, as shown in FIG. 9, the rear face 22 of the gripping portion 9 is aligned with the rear surface 5 in such a way as to form, in its entirety, a continuous surface.

It should also be noted that the gripping portion 9 inserted in the track 30 is preferably aligned with the rear surface 11 of the supporting base 1. In other words, the gripping portion 9 has a relative outer side facing towards the outside of the supporting layer 3 (in a direction opposite to the front surface 4); at the outer side the gripping portion 9 is aligned with the rear surface 5 in such a way as to substantially form a continuous surface.

In other alternative embodiments, the gripping portion 9 is inserted in the track and protrudes from the rear surface 5 with its outer side for a predetermined height.

Alternatively, the gripping portion 9 could be completely inserted in the track 30 and form a recess relative to the rear surface 5. In other words, the gripping portion 9 is not flush with the rear surface 5 and forms a step relative to the rear surface 5.

Figure 8:
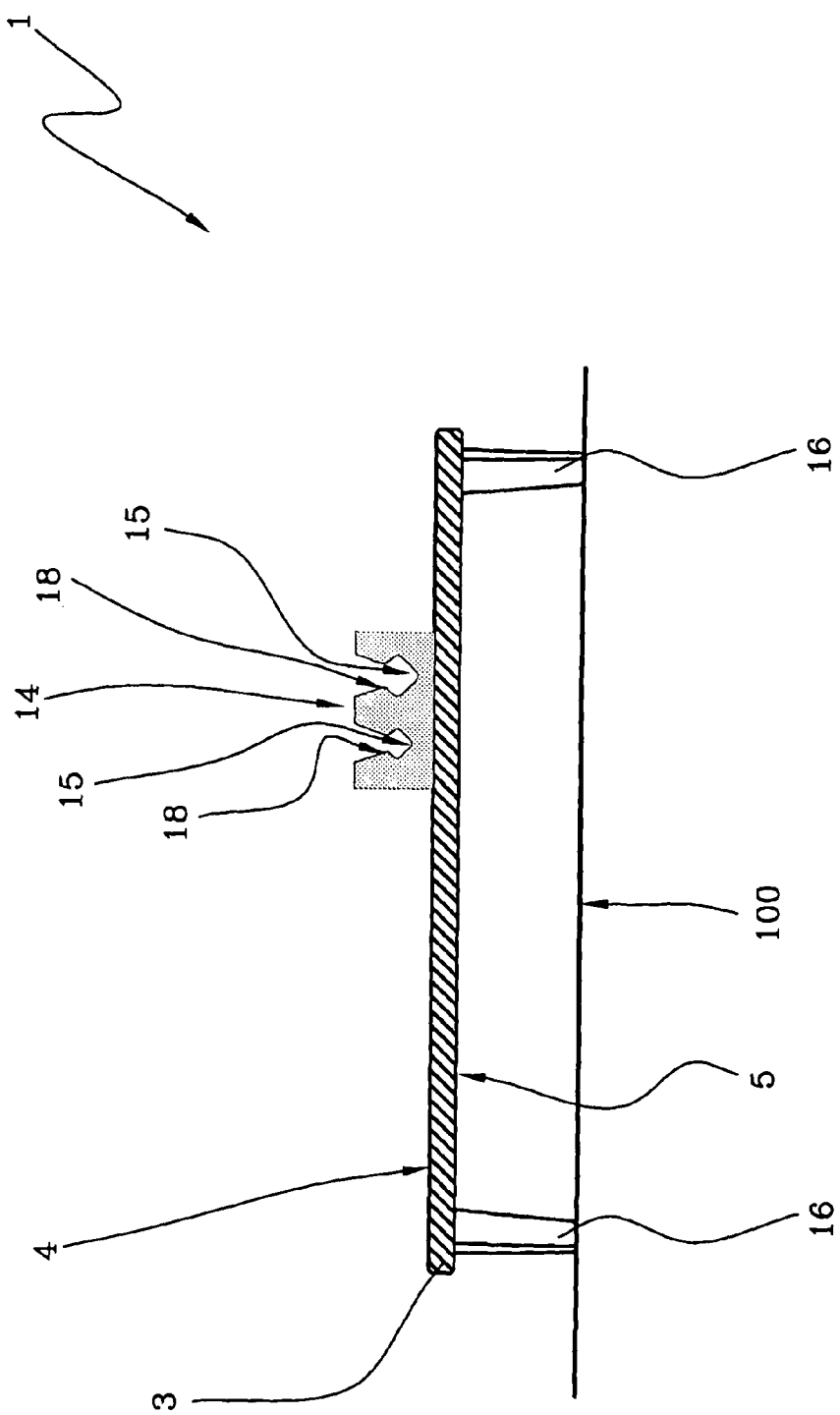
FIG. 8 is a side view of the supporting base of FIG. 7 in a cross-section through the line VIII-VIII.

In the second embodiment illustrated in the accompanying drawings (in particular in FIGS. 8 and 9), the gripping portion 9 rises from the front surface 4 in such a way as to form the protruding gripping portion 14. The protruding gripping portion 14 rises from the front surface 4 and is shaped to define at least one cavity 15 for containing a medical instrument 2. More in detail, FIG. 8 shows that the gripping portion 14 forms two containment cavities 15 alongside each other.

In that way, it is possible to define at least one cavity 15 for containing a medical instrument 2 in a raised position relative to the front surface 4. More specifically, the protruding gripping portion 14 has a top wherein each containment cavity 15 is made. Preferably, the containment cavity 15 has an extension substantially parallel to the front surface 4 in such a way as to contain a medical instrument 2 positioned along the extension.

It should be noted that the gripping portion 14 has, at the top, a guide profile 18 placed in communication with the containment cavity 15. More specifically, the guide profile 18 is shaped like an inverted truncated cone to favour the insertion of a medical instrument 2 in the containment cavity 15. The guide profile 18 extends between an upper opening (for the entrance of the medical instrument 2) and a lower opening having a diameter less than the upper opening. More in detail, the lower opening is interposed between the rest of the guide profile 18 and the containment cavity 15 and forms a narrowing of the cross section relative to the containment cavity 15 in such a way as to hold the medical instrument 2 in position once it has passed the lower opening.

As for the first embodiment, the second embodiment contemplates that the supporting layer 3 and the gripping portion 9 are co-pressed together in such a way as to form a single body. It should be noted that the plastic of the supporting layer 3 and the silicone of the gripping portion 9 lend themselves to the co-pressing technique.

As already mentioned, the supporting layer 3 and the gripping portion 9 are joined together by means of known techniques which allow the irreversible joining of two materials (for example: casting, etc.)

Lastly, as shown in FIGS. 8, 9 and 11, the supporting base 1 comprises the supporting means 16 connected to the supporting layer 3 and extending away from it in such a way as to support the rest of the supporting base 1.

Preferably, the supporting means 16 comprise a plurality of supporting feet extending away from the supporting layer 3 for a predetermined length in such a way as to support the supporting layer 3.

This invention also relates to a method for making a supporting base 1 for medical instruments 2. More specifically, for the description of the method reference should be made to the previous description for the supporting base 1.

Moreover, the method comprises a first operating step of preparing a supporting layer 3 of the type described previously. As mentioned, the supporting layer 3 is preferably made from plastic.

Then, the method comprises a second operating step which comprises making a plurality of holes passing through the supporting layer 3 from the front surface 4 to the rear surface 5.

Moreover, the method comprises preparing a gripping portion 9. As mentioned, the gripping portion 9 is preferably made of silicone. In that case, the silicone is positioned on the supporting material 3 and left to solidify.

Moreover, the method comprises joining the gripping portion 9 to the supporting layer 3 only at the rear surface 5. Preferably, after the joining step, the gripping portion 9 has propagated inside the holes 6 in such a way as to form the protuberances 13.

After the step of joining, the method comprises a step of making holes in at least part of the gripping portion 9 as an extension of a respective hole of the supporting layer 3 in such a way as to make the opening 17 as described above. In that way, the perforated gripping portion 9 defines an annular gripping surface for a medical instrument 2 inserted in the opening 17.

More in detail, the step of making holes comprises making the openings 17 inside a respective protuberance 13 of the gripping portion 9. Preferably, the step of making holes is performed by making one or more cuts in such a way as to make the opening 17 according of the predetermined design specifications.

In a variant of this embodiment of the method, it is possible to make the hole 6 and the respective opening 17 with a single cutting operation after joining the gripping portion 9 with the supporting layer 3.

Alternatively, it is possible to implement, following the step of making a plurality of holes 6 passing through the supporting layer 3, a step of positioning the supporting layer 3 in a mould having the protrusions positioned at the openings 17 to be created. Following the positioning step, the method comprises a step of positioning the gripping portion 9 on the supporting layer 3 in such a way that the gripping portion 9 enters into the holes 6 and it adapts to the shape defined by the protrusions of the mould.

Then, the method comprises leaving the gripping portion 9 to solidify and proceeding with the joining step. In that way, the openings 17 are created simultaneously with the joining step.

This alternative is preferably actuated using silicone for the gripping portion 9.

Preferably, the step of joining the gripping portion 9 to the supporting layer 3 is carried out by co-pressing.

Moreover, the method may comprise a final step of finishing the openings 17 which comprises shaping the inner surface of each opening 17 according to the design requirements.

In addition, the method may comprise a step of smoothing the front surface of the supporting layer 3 in such a way as to make it smoother. The smoothing operation can be actuated during the manufacture of the supporting layer 3 or after the manufacture of the supporting layer 3.

The smoothing operation is favoured since the gripping portion 9 is joined to the supporting layer 3 only at the rear surface 5 and, therefore, the front surface 4 is not made of gripping material.

According to the second embodiment illustrated in FIGS. 7 to 11, the method comprises placing the gripping portion 9 on the rear surface 5 along the predetermined path. In addition, the gripping portion 9 is positioned in the holes 6 of the group 31 in such a way as to fill them.

More specifically, the method comprises a step of cutting on the supporting layer 5 at least one track 30 extending along a predetermined path and passing through at least one group 31 of holes 6 in order to place them in communication with each other through the track 30. In other words, the method comprises making a cut on the rear surface 5 in such a way as to create a space for introducing the gripping portion 9. As described above, this invention comprises making a plurality of cuts passing through respective groups 31 of holes 6 or making a single cut passing through all the holes 6 of the supporting layer 3.

Preferably, the step of positioning the gripping portion 9 on the rear surface 5 is implemented by positioning the gripping portion 9, at least in part, inside the track 30 and at the group 31 of holes 6 in such a way as to fill the track 30 and the holes 6 with the gripping portion 9.

More in detail, the gripping portion 9 is positioned along the track 30 and at the group 31 of holes in such a way as to fill the track 30 and the holes 6 with the gripping portion 9. In other words, this step comprises positioning the gripping portion 9 in the track 30 and positioning the gripping portion 9 in the holes 6 positioned along the track 30. More specifically, the method comprises joining the gripping portion 9 to the supporting layer 3. Preferably, this step is carried out together with the step of positioning the gripping portion 9 along the track 30 and at each hole of the group 31.

Moreover, the method comprises a step of making at least one opening 17 at each hole 6 and passing through the gripping portion 9 for inserting, in use, at least one medical instrument 2.

Preferably, the step of positioning the gripping portion 9 along the track 30 is implemented by injecting gripping material at least at one injection point 32 positioned along the track 30. The gripping material is preferably in the semi-solid or liquid state so as to introduce itself along the track 30. Preferably, the gripping material is injected at some parts of the track 30. In effect, the track 30 comprises extensions 33 extending at areas where there are no holes 6 and suitable for injection of the gripping material. That way, the gripping material after it has been injected expands along the rest of the track 30.

Moreover, the method comprises the steps of inserting the gripping portion 9 in the track 30 and in each hole 6. In addition, the step of inserting comprises the sub-step of joining the gripping portion 9 to the rear surface 5 and the annular inner surface 20 of the supporting layer 3 in such a way as to obtain a single body.

More specifically, the step of joining the gripping portion 9 to the supporting layer 3 occurs by co-pressing the gripping portion 9 (preferably made of silicone) with the supporting layer 3 (preferably made of plastic). In general, the gripping portion 9 and the supporting layer 3 are made of materials suitable for mutual co-pressing.

In practice, the step of positioning the gripping portion along the track 30 is carried out as follows:
preparing the gripping material in a semi-solid state;
filling the track 30 and the holes 6 with the gripping material;
leaving the gripping material to solidify in the holes 6;
cutting the gripping portion 9 solidified in the holes 6 to form the openings 17.

Alternatively, before the sub-step of filling the track 30 and the holes 6 with gripping material, it is possible to implement a step of positioning the supporting layer 3 in a mould having the protrusions positioned at the openings 17 to be created. In that way, the gripping portion enters into the holes 6 and adapts to the shape defined by the protrusions of the mould in such a way as to directly make the openings 17.

Then, the method comprises leaving the gripping material to solidify. In that way, the openings 17 are created simultaneously with the solidification step.

Moreover, the method may comprise a final step of finishing the openings 17 which comprises shaping each opening 17 according to the design requirements.

In addition, the method may comprise a step of smoothing the front surface 4 and the rear surface 5 of the supporting layer 3 in such a way as to make it smoother. The smoothing operation can be actuated during the manufacture of the supporting layer 3 or after the manufacture of the supporting layer 3.

This invention achieves the preset aims.

More specifically, the irreversible joining of the supporting layer with the gripping portion eliminates the gaps which are usually created between the sealing rings and the supporting layer. This prevents the introduction and accumulation of dirt in the gaps so as to keep the supporting base even cleaner.

Moreover, the presence of the gripping portion joined to the supporting layer at the track and the holes makes it possible to obtain a front surface and a rear surface free from obstacles and easy to clean.

More specifically, with regards to the rear surface, the gripping portion is only present along the track and at the holes. Whilst, with regards to the front surface, the gripping portion is only present at the holes. In that way, the majority of the front and rear surfaces is formed by the supporting base which is usually made of material which is smooth and easy to clean. In addition, it is important to note that the presence of the gripping portion joined to the supporting layer only at the track and the annular inner surface, facilitates the gripping of the medical instruments by an operator (with the fingers of one hand) as the latter operates on the front surface where the gripping material is located only around the holes. On the other hand, the presence of gripping material on the front surface would make it difficult (due precisely to the intrinsic nature of the gripping material) for the fingers of the operator to slide on the front surface for gripping the medical instruments. This problem would be even more evident in the frequent case in which the operator works with latex gloves and the gripping material is made of silicone.

Moreover, the presence of the gripping portion positioned only at the openings makes the front surface more shiny.

In addition, the presence of the gripping portion joined to the supporting layer at the annular inner surface facilitates operations for design (for example by silk screen process and/or pad printing and/or laser marking) of the front surface to distinguish, using colours and/or symbols, the various holes or groups of holes on the supporting base.

It should also be noted that the presence of the tracks facilitates the positioning of the gripping material at the holes since the predetermined path of each track in itself leads the gripping material along the desired areas.

Moreover, the use of the tracks allows a reduction in the quantity of gripping material used to create the gripping areas in the holes. In effect, the gripping material is positioned only inside the tracks and in the respective holes.

Lastly, it should be noted that it is possible to select the shape of the inner surface of the openings advantageously in order to facilitate the operations for cleaning/sterilising the openings. For example, a star or oval shape extends the spaces within the opening to facilitate cleaning/sterilising operations without affecting the dimensions of the area for retaining the medical instrument.

It should also be noticed that this invention is relatively easy to produce and that even the cost connected with implementing the invention is not very high.

The invention claimed is:

1. A method for making a supporting base (1) for medical instruments (2), comprising the following operating steps:
   preparing a supporting layer (3) comprising its own visible front surface (4) and its own rear surface (5) opposite to the visible surface (4);
   making a plurality of holes (6) through the supporting layer (3) from the front surface (4) to the rear surface (5);
characterized in that the method comprises the steps of:
   cutting on the rear surface (5) at least one track (30) extending along a predetermined path passing through at least one group (31) of holes (6) in order to place them in communication with each other through the track (30);
   injecting gripping material at least at one injection point (32) positioned along the track (30) on the rear surface (5) in such a way to position a gripping portion (9), at least in part, inside the track (30) and at the group (31) of holes (6) in such a way as to fill the track (30) with the gripping material realizing a gripping portion (9) on the rear surface (5); the gripping material being in the semi-solid or liquid state for introduction and expansion along the track (30) in the rear surface (5) and inside at least part of the holes (6) of the group (31) in such a way as to fill said at least part of the holes (6);
   leaving the gripping material to solidify and waiting for the solidification of the gripping material on the rear surface (5) in such a way to realize an irreversible joining of the gripping portion (9) to the rear surface (5) to form a single body with the supporting layer (3) to prevent dirt from entering between the supporting layer (3) and the gripping portion (9);
   making at least one opening (17) at each hole (6) and passing through the gripping portion (9) for inserting, in use, at least one medical instrument (2) in such a way that the gripping portion (9) defines a gripping area for the medical instrument (2).

2. The method according to claim 1 characterized in that the step of cutting on the rear surface (5) at least one track (30) comprises a sub-step of realizing extensions (33) of the track (30) where there are no holes (6); the step of injecting gripping material being realized at one of the extensions (33).

3. The method according to claim 1 characterized in that the step of making at least one opening (17) at each hole (6) is realized by cutting the gripping portion (9) solidified in the hole (6).

4. The method according to claim 1 characterized in that the step of making at least one opening (17) at each hole (6) is realized by positioning, before the step of filling the track (30) and the holes (6) with gripping material, the supporting layer (3) in a mould having protrusions positioned at the openings (17) to be created in such a way that the openings are created simultaneously with the solidification step.

5. The method according to claim 1 characterized by comprising a step of shaping each opening (17) according to predetermined design requirements.

6. The method according to claim 1 characterized in that the method comprises a step of smoothing the front surface (4) and the rear surface (5) of the supporting layer (3) in such a way to make the supporting layer (3) smoother.

7. The method according to claim 1, characterized in that the step of cutting on the rear surface (5) at least one track (30) comprises a sub-step of cutting a plurality of tracks (30) separate from each other associated with respective groups (31) of holes (6) in such a way that each track (30) places in communication the holes (6) of a respective group (31).

8. The method according to claim 1, characterized in comprising a step of aligning a rear face (22) of the gripping portion (9) inserted in the track (30) with the rear surface (5) at a relative outer side facing towards the external environment so as to form substantially a continuous surface.

9. The method according to claim 1, characterized in comprising a step of aligning a front face (21) of the gripping portion (9) with the front surface (4) so as to form, overall, a continuous surface; said gripping portion (9) extending along the hole (6) from its own rear face (22), positioned at the rear surface (5), to its own front face (21) positioned at the front surface (4).

10. The method according to claim 1, characterized in that the supporting layer (3) is realized by using plastic material.

11. The method according to claim 1, characterized in that the gripping portion (9) is realized in rubber.

12. The method according to claim 1, characterized in that the step of making at least one opening (17) at each hole (6) comprises making a plurality of separate openings (17) through the gripping portion (9) of a single hole (6) for the insertion of a medical instrument (2) for each separate opening (17).

13. The method according to claim 1, characterized in that the method comprises a step of realizing a raised gripping portion (9) above the front surface (4) in such a way as to form a gripping portion (14) projecting above the front surface; the step of realizing said gripping portion (14) comprising a sub-step of shaping said gripping portion (14) to form at least one cavity (15) for containing a medical instrument (2) in a position raised relative to the front surface (4).

14. The method according to claim 1, characterized in that the step of joining the gripping portion (9) to the supporting layer (3) is carried out by co-pressing.

15. The method according to claim 1, characterized in that the gripping portion (9) is realized in silicone rubber.

* * * * *